(12) United States Patent
Hirata et al.

(10) Patent No.: US 12,337,468 B2
(45) Date of Patent: Jun. 24, 2025

(54) JOINT FUNCTION UNIT

(71) Applicant: NHK SPRING CO., LTD., Kanagawa (JP)

(72) Inventors: Takafumi Hirata, Kanagawa (JP); Yuki Hotoda, Kanagawa (JP); Masahiro Inaba, Kanagawa (JP)

(73) Assignee: NHK SPRING CO., LTD., Kanagawa (JP)

( * ) Notice: Subject to any disclaimer, the term of this patent is extended or adjusted under 35 U.S.C. 154(b) by 0 days.

(21) Appl. No.: 18/015,537

(22) PCT Filed: Jul. 14, 2021

(86) PCT No.: PCT/JP2021/026388
§ 371 (c)(1),
(2) Date: Jan. 11, 2023

(87) PCT Pub. No.: WO2022/014628
PCT Pub. Date: Jan. 20, 2022

(65) Prior Publication Data
US 2023/0256625 A1 Aug. 17, 2023

(30) Foreign Application Priority Data

Jul. 16, 2020 (JP) ................................. 2020-122343

(51) Int. Cl.
*B25J 17/02* (2006.01)
*A61B 34/30* (2016.01)

(52) U.S. Cl.
CPC ............... *B25J 17/02* (2013.01); *A61B 34/30* (2016.02); *A61B 2034/305* (2016.02)

(58) Field of Classification Search
CPC ........................ A61B 34/71; A61B 2034/715
See application file for complete search history.

(56) References Cited

U.S. PATENT DOCUMENTS 5,179,935 A * 1/1993 Miyagi ................ A61B 1/0055
600/150
9,005,112 B2 * 4/2015 Hasser .................. A61B 1/008
600/102
(Continued)

FOREIGN PATENT DOCUMENTS

CN 101820824 9/2010
CN 105473095 4/2016
(Continued)

OTHER PUBLICATIONS

"International Preliminary Report on Patentability of PCT/JP2021/026388; this report contains the following items: Form PCT/IB/326, PCT/IB/338, PCT/IB/373, PCT/ISA237(cover sheet), PCT/ISA237(Box No. I), PCT/ISA237(Box No. V)", mailed on Jan. 26, 2023, Jan. 17, 2023, Sep. 28, 2021, which is English translation of "Written Opinion of the International Searching Authority", p. 1-p. 10.

(Continued)

*Primary Examiner* — T. Scott Fix
(74) *Attorney, Agent, or Firm* — JCIPRNET

(57) ABSTRACT

A joint function unit, in which a movable part is supported by a base part so as to be displaceable in an axial direction thereof, includes: a plurality of drive wires each having a fixed part fixed to the movable part on one side in the axial direction and a supported part supported by the base part on the other side in the axial direction; and an elastic body supporting the supported part of each of the plurality of drive wires on the base part, energizing the supported part with respect to the fixed part in the axial direction, and applying tension to the drive wires.

10 Claims, 10 Drawing Sheets

(56) References Cited

U.S. PATENT DOCUMENTS

| | | | |
|---|---|---|---|
| 9,545,727 | B1 | 1/2017 | Shamlian et al. |
| 10,321,900 | B2 | 6/2019 | Au et al. |
| 2001/0023313 | A1* | 9/2001 | Ide .................... A61B 1/0057 |
| | | | 600/142 |
| 2012/0310253 | A1 | 12/2012 | Choi et al. |
| 2015/0087905 | A1* | 3/2015 | Ueda .................... A61B 1/0057 |
| | | | 604/95.04 |
| 2015/0289942 | A1 | 10/2015 | Au et al. |
| 2017/0129110 | A1 | 5/2017 | Ohm et al. |
| 2019/0240478 | A1 | 8/2019 | Halpern et al. |

FOREIGN PATENT DOCUMENTS

| | | |
|---|---|---|
| CN | 105636545 | 6/2016 |
| CN | 107073723 | 8/2017 |
| CN | 109562523 | 4/2019 |
| EP | 2211733 | 8/2010 |
| EP | 2361170 | 8/2018 |
| JP | 2009538186 | 11/2009 |
| JP | 2015156906 | 9/2015 |
| WO | 2011040369 | 4/2011 |
| WO | 2016129336 | 8/2016 |

OTHER PUBLICATIONS

"International Search Report (Form PCT/ISA/210) of PCT/JP2021/026388," mailed on Sep. 28, 2021, with English translation thereof, pp. 1-4.
"Search Report of Europe Counterpart Application", issued on Nov. 21, 2023, p. 1-p. 9.
"Office Action of Taiwan Counterpart Application", issued on Sep. 6, 2024, with partial English translation thereof, pp. 1-7.
"Office Action of China Counterpart Application", issued on Feb. 25, 2025, with English translation thereof, p. 1-p. 15.

* cited by examiner

JOINT FUNCTION UNIT

CROSS-REFERENCE TO RELATED APPLICATION

This application is a 371 application of the International PCT application serial no. PCT/JP2021/026388, filed on Jul. 14, 2021, which claims the priority benefit of Japan Patent Application No. 2020-122343, filed on Jul. 16, 2020. The entirety of each of the above-mentioned patent applications is hereby incorporated by reference herein and made a part of this specification.

TECHNICAL FIELD

The present invention relates to a joint function unit provided for a robot, a manipulator, or the like.

RELATED ART

Some robots, manipulators or actuators have a joint function unit that enables bending and extension. Examples of such a joint function unit include one described in Patent Document 1 which is applied to a surgical instrument.

In this joint function unit, an end effector being a movable-side member is joined to a pipe being a fixed-side member by a bendable member.

One side of an actuation cable being a cord-like member is fixed to the end effector. By pulling the other side of the actuation cable, it is possible to bend the bendable member and displace the end effector with respect to an axis.

However, in the above-mentioned conventional joint function unit, when an external force is applied to the end effector or the like, the bendable member may be forced to bend, and unintended displacement of the end effector may be caused.

PRIOR-ART DOCUMENTS

Patent Documents

Patent Document 1: Japanese Translation of PCT International Application Publication No. 2009-538186

SUMMARY OF THE INVENTION

Problems to be Solved by the Invention

A problem to be solved is that unintended displacement of a movable-side member occurs due to an external force.

Means for Solving the Problems

The present invention is a joint function unit in which a movable-side member is supported so as to be displaceable between a bending position and an extension position with respect to a fixed-side member. The joint function unit is most characterized by including: a plurality of cord-like members, having a fixed part fixed to the movable-side member on one side in an axial direction and a supported part supported by the fixed-side member on the other side in the axial direction; and an elastic body, supporting the supported part of the plurality of cord-like members on the fixed-side member, energizing the supported part toward a side opposite to the fixed part in the axial direction, and applying tension to the cord-like member.

Effects of the Invention

According to the present invention, since looseness in the cord-like member is eliminated by the tension applied by the elastic body, and bending rigidity of the joint function unit is improved, even if an external force acts on the movable-side member, unintended displacement of the movable-side member can be suppressed.

Figure 1:
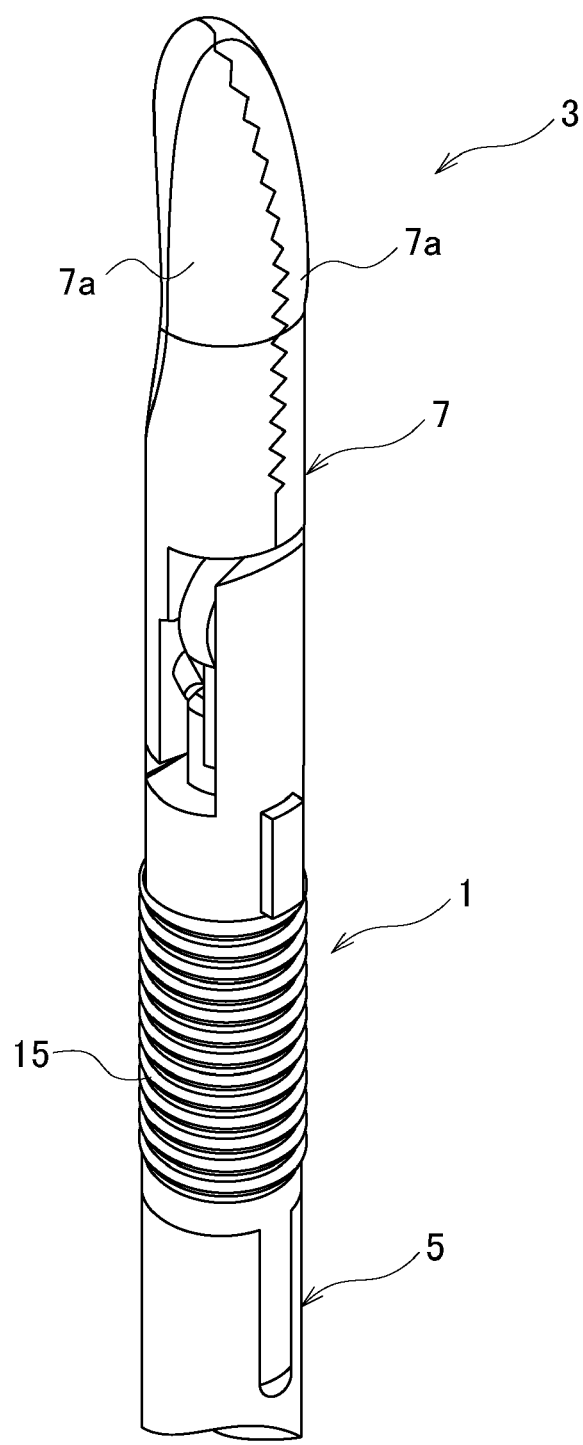
FIG. 1 is a perspective view showing a main part of a manipulator to which a joint function unit according to Embodiment 1 of the present invention is applied.
Figure 4:
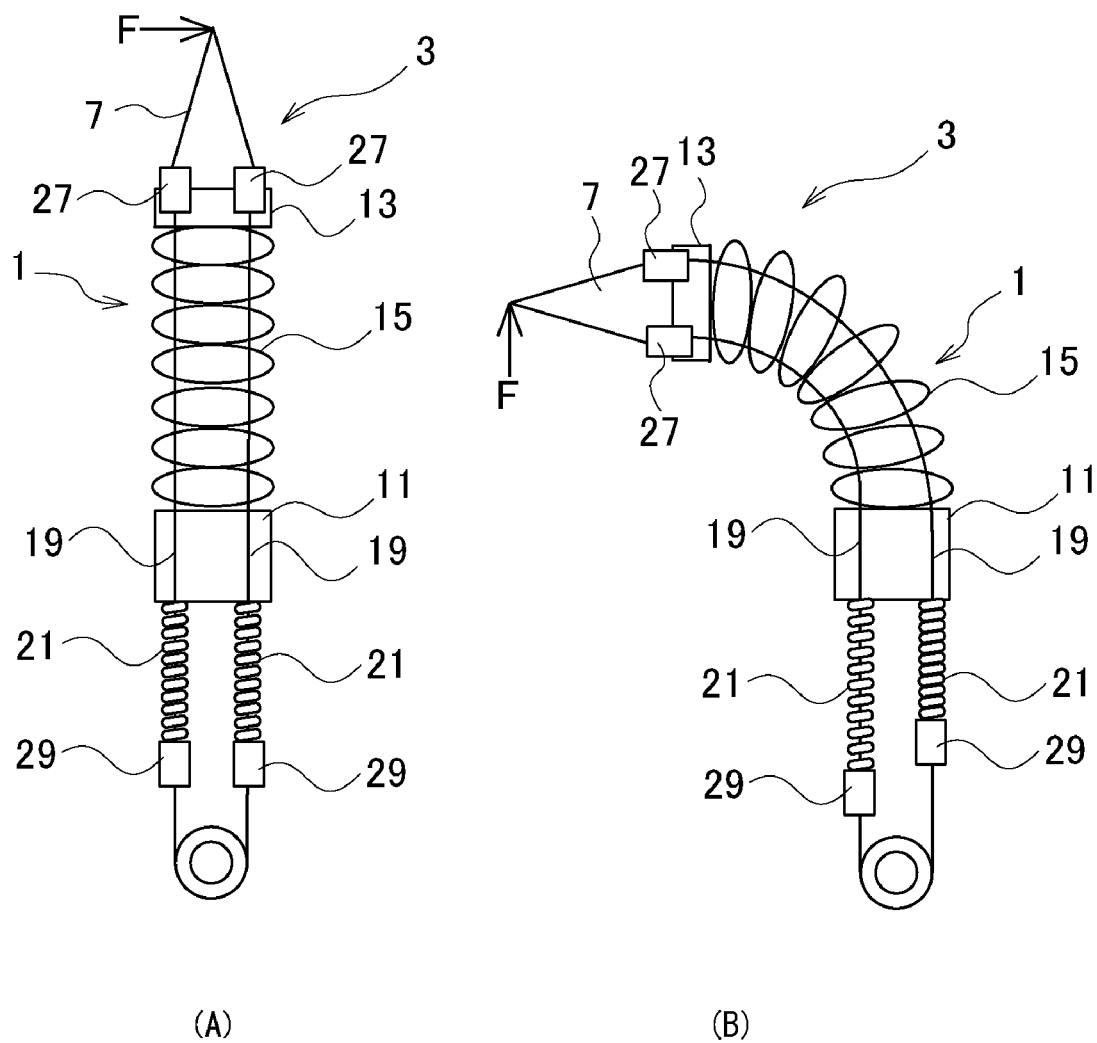

(A) and (B) of FIG. 4 are conceptual views of the manipulator of FIG. 1, in which (A) of FIG. 4 shows a normal state and (B) of FIG. 4 shows a bending state.

Figure 5:
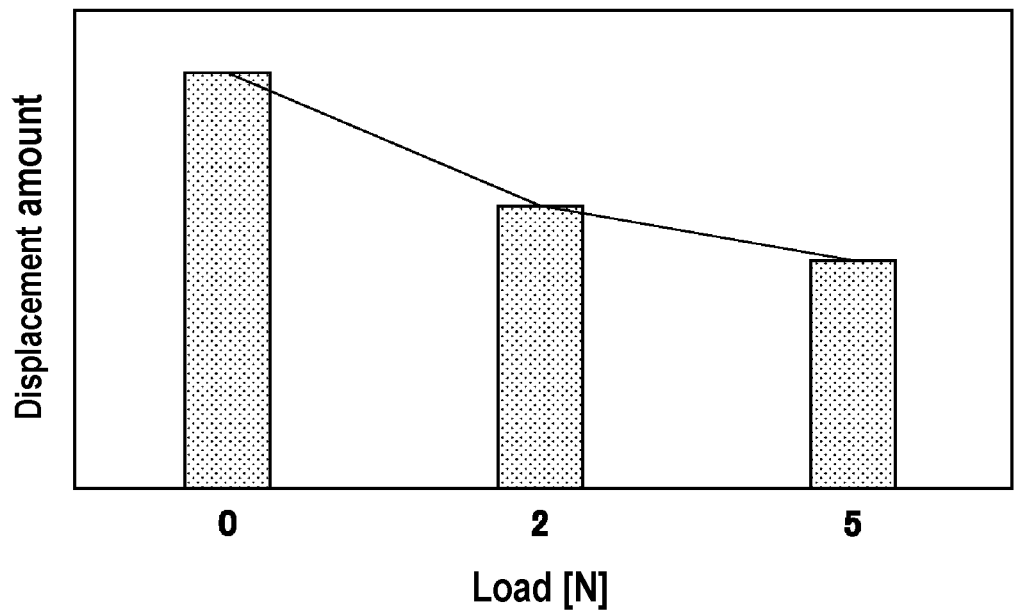

FIG. 5 is a graph showing a relationship between displacement amount with respect to external force and load of an elastic body.

Figure 6:
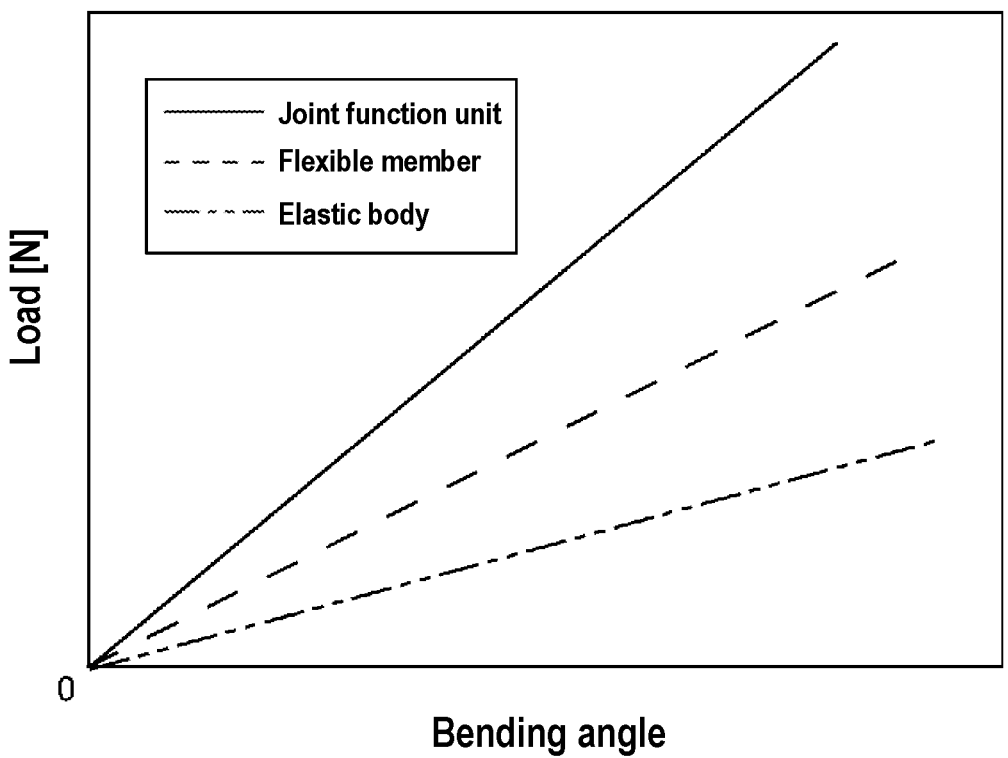

FIG. 6 is a graph showing a relationship between load and bending angle of a joint function unit.

Figure 7:
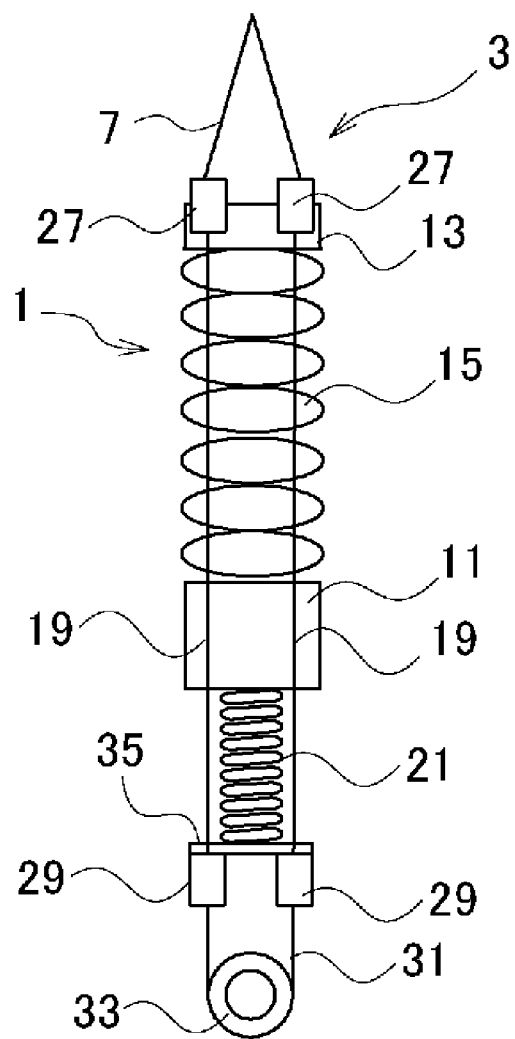

FIG. 7 is a conceptual view showing a manipulator to which a joint function unit according to Embodiment 2 of the present invention is applied.

Figure 8:
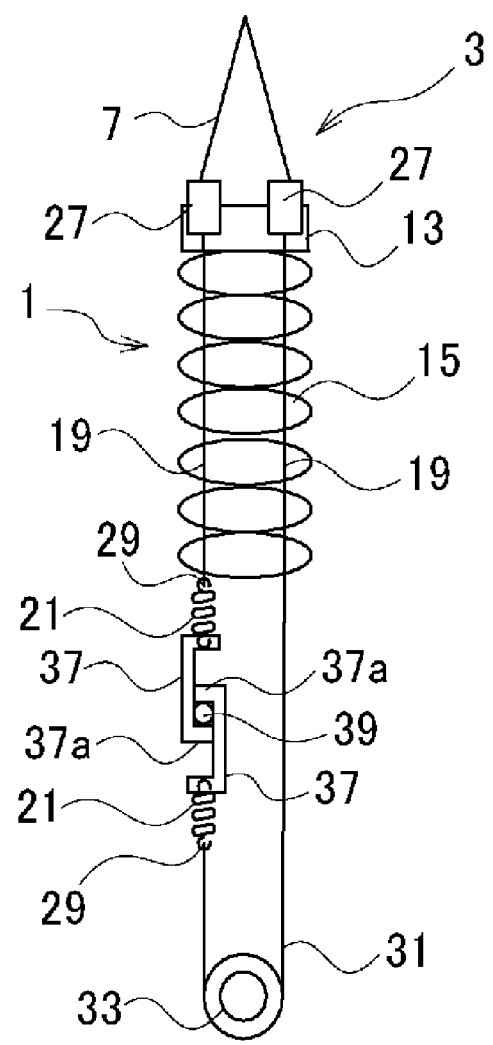

FIG. 8 is a conceptual view showing a manipulator to which a joint function unit according to Embodiment 3 of the present invention is applied.

Figure 9:
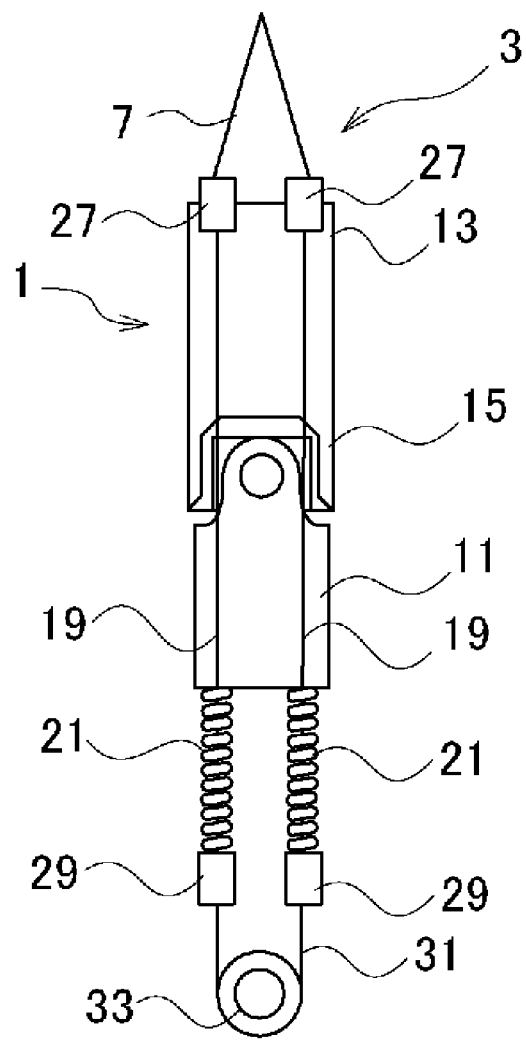

FIG. 9 is a conceptual view showing a manipulator to which a joint function unit according to Embodiment 4 of the present invention is applied.

Figure 10:
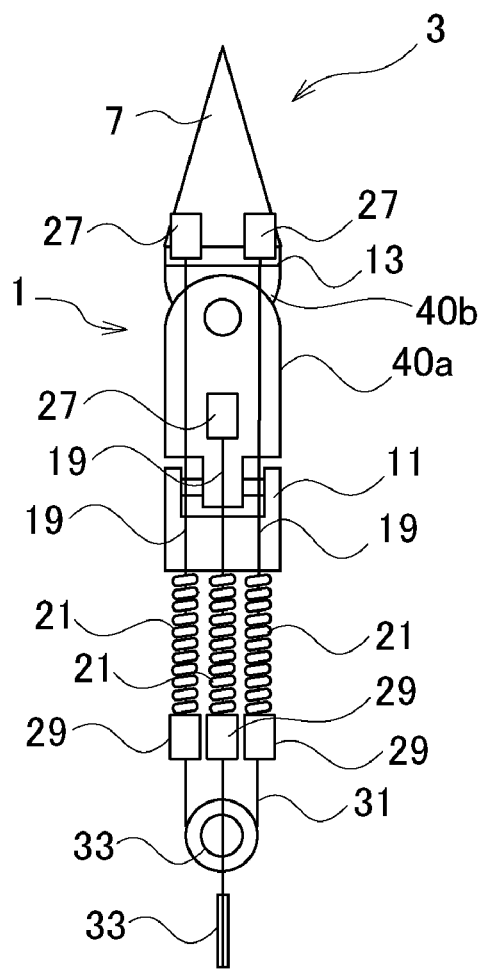
Figure 10:
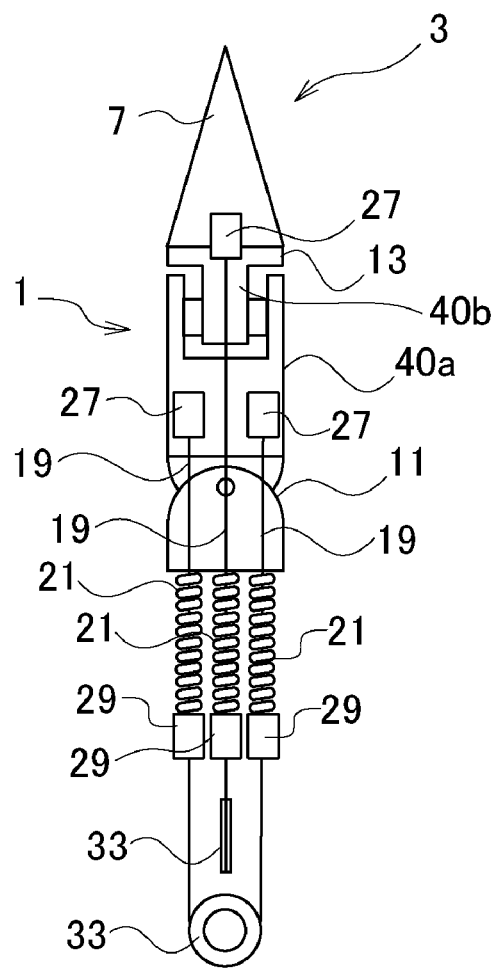

(A) of FIG. 10 is a conceptual view showing a manipulator to which a joint function unit according to a modification of Embodiment 4 of the present invention is applied, and (B) of FIG. 10 is a conceptual view of (A) of FIG. 10 as seen from a direction 90 degrees different from that of (A) of FIG. 10.

Figure 11:
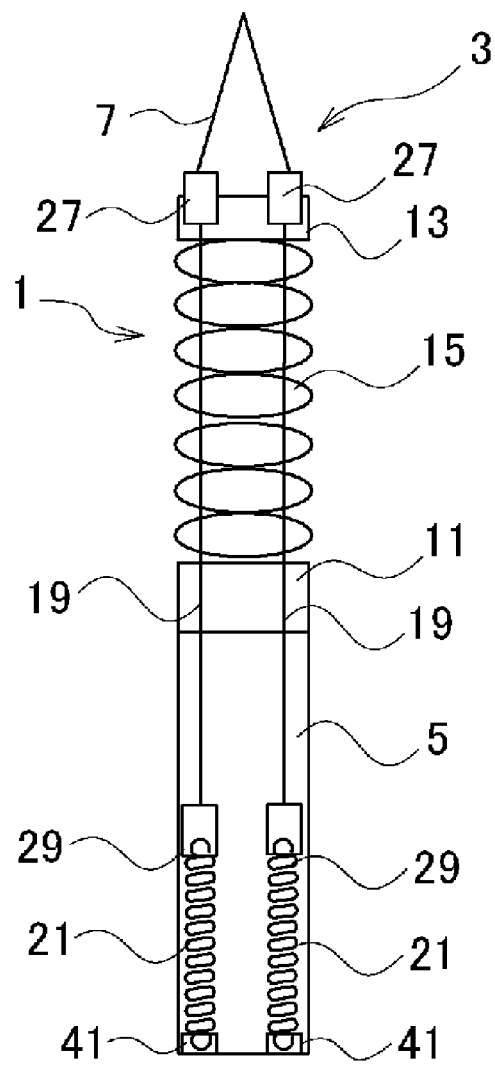

FIG. 11 is a conceptual view showing a manipulator to which a joint function unit according to Embodiment 5 of the present invention is applied.

DESCRIPTION OF THE EMBODIMENTS

The purpose of suppressing unintended displacement of a movable-side member is achieved by applying tension, by an elastic body, to a cord-like member for displacing the movable-side member.

That is, a joint function unit (1) is provided in which a movable-side member (13) is supported so as to be displaceable between a bending position and an extension position with respect to a fixed-side member (11), and the joint function unit (1) includes a plurality of cord-like members (19) and an elastic body (21). The cord-like member (19) has a fixed part (27) fixed to the movable-side member (13) on one side in an axial direction and a supported part (29) supported by the fixed-side member (11) on the other side in the axial direction. The elastic body (21) supports the supported part (29) of the plurality of cord-like members (19) on the fixed-side member (11), energizes the supported part (29) toward a side opposite to the fixed part (27) in the axial direction, and applies tension to the cord-like member.

The elastic body (21) may be configured to be arranged in parallel with the plurality of cord-like members (19).

The plurality of cord-like members (19) may each be configured to be inserted through the fixed-side member (11) between the fixed part (27) and the supported part (29). The elastic body (21) may be configured to be interposed between the supported part (29) of the plurality of cord-like members (19) and the fixed-side member (11).

The elastic body (21) may be configured to have each of the plurality of cord-like members (19) inserted therethrough and provided on the same axis.

The joint function unit (1) may be configured to include a support member (35) spanning between the supported parts (29) of the plurality of cord-like members (19). The elastic body (21) may be configured to be interposed between the support member (35) and the fixed-side member (11).

The joint function unit (1) may be configured to include a guide part (33) that guides one of the plurality of cord-like members (19) and locates the supported part (29) of the plurality of cord-like members (19) on the same axis. The elastic body (21) may be configured to connect between the supported parts (29) of the plurality of cord-like members (19).

The fixed-side member (11) may be configured to include a support part (41) located on a side opposite to the fixed part (27) with the supported part (29) of the plurality of cord-like members (19) therebetween in the axial direction. The elastic body (21) may be configured to be interposed between the support part (41) and the supported part (29) of the plurality of cord-like members (19).

The elastic body (21) may be a coil spring.

The cord-like member (19) may be a drive wire in which the supported part (29) is operated in the axial direction to displace the movable-side member (13) with respect to the fixed-side member (11). However, the cord-like member may be provided separately from the drive wire.

Embodiment 1

[Manipulator]

Figure 2:
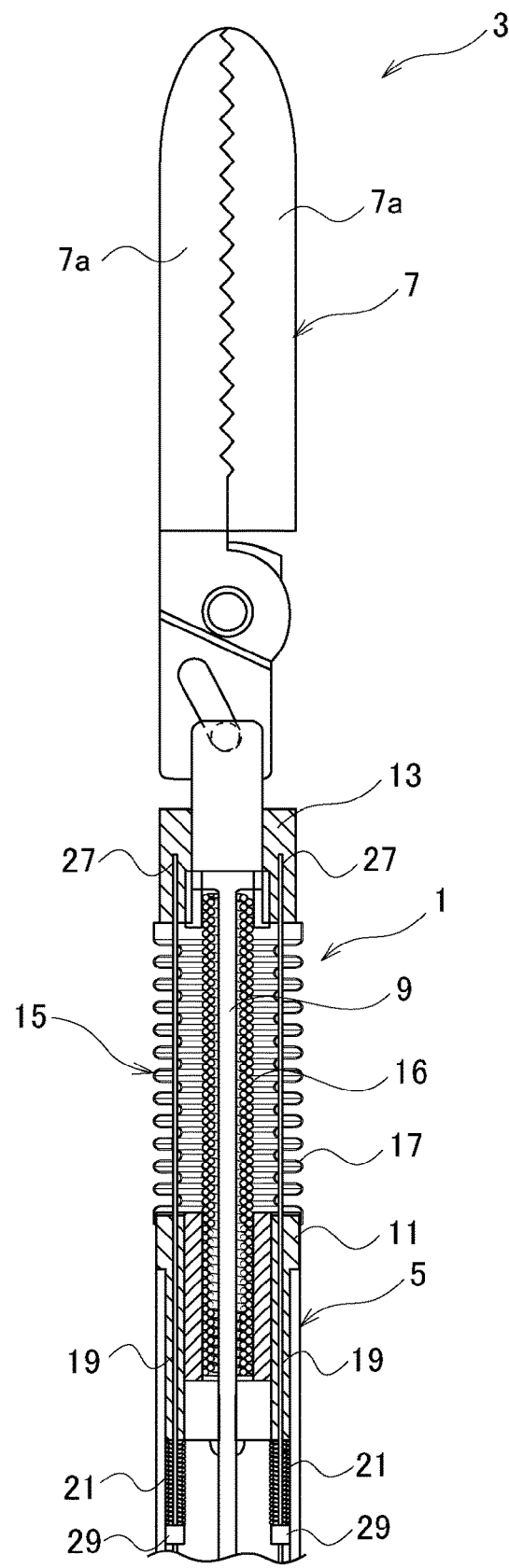
FIG. 2 is a sectional view of the manipulator of FIG. 1.
Figure 3:
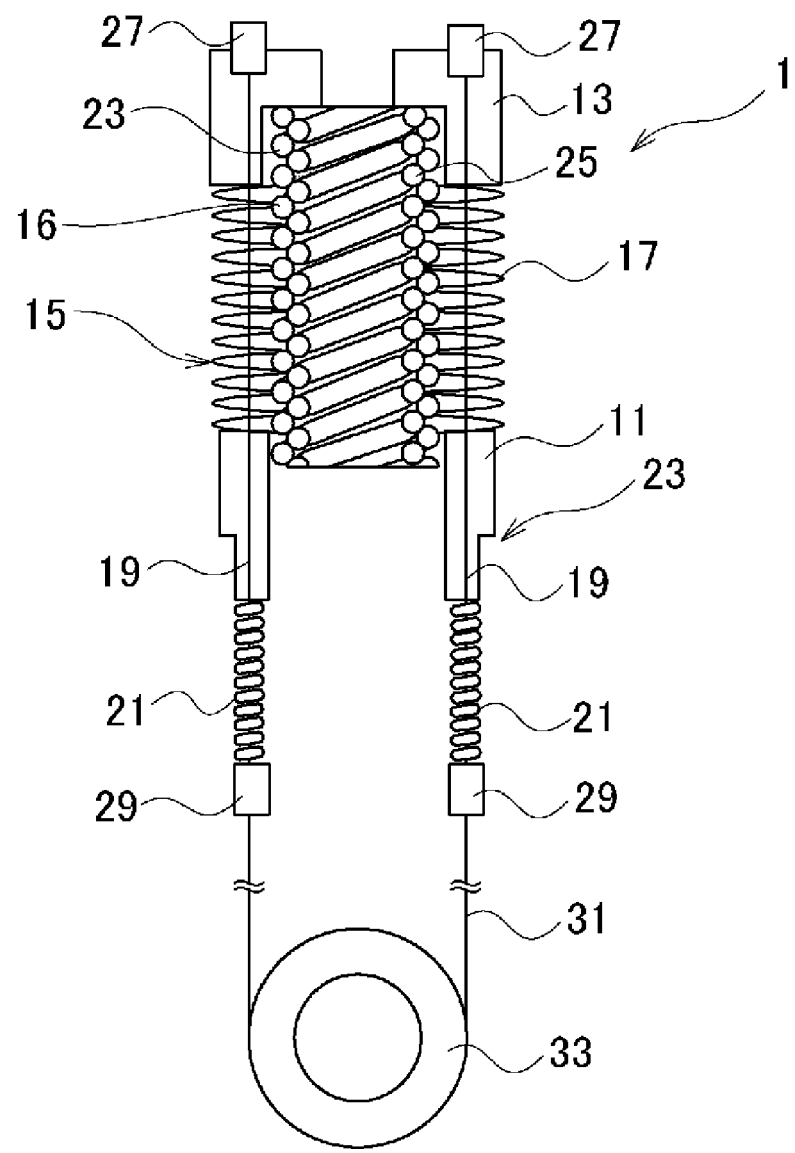
FIG. 3 is a schematic view showing a main part of FIG. 2.

FIG. 1 is a perspective view showing a main part of a manipulator to which a joint function unit according to Embodiment 1 of the present invention is applied, FIG. 2 is a sectional view of the manipulator of FIG. 1, and FIG. 3 is a schematic view showing a main part of FIG. 2.

In the present embodiment, a manipulator 3 is described as an example of a device having a joint function unit 1. The manipulator 3 is a forceps for medical use, and may be used not only as a forceps attached to a surgical robot, but also as an endoscopic camera or manual forceps not attached to a surgical robot.

It suffices if the device having the joint function unit 1 is a device requiring a joint function, and the device may be a robot, manipulator, actuator or the like in various fields. The manipulator 3 includes a shaft 5, the joint function unit 1, and an end effector 7.

The shaft 5 is formed in, for example, a cylindrical shape. The end effector 7 is movably supported on a tip side of the shaft 5 via the joint function unit 1. The joint function unit 1 will be described later.

The end effector 7 is a forceps for medical use, and is pivotally supported with respect to a movable part 13 of the joint function unit 1 to be described later so that a pair of grippers 7a are able to open and close. The end effector 7 is connected to a push-pull cable 9 inserted through the shaft 5 and the joint function unit 1. The grippers 7a are configured to open and close according to an axial movement (advance or retreat) of the push-pull cable 9.

The grippers 7a may be driven by air or the like. The end effector 7 may be something other than a forceps, such as scissors, a gripping retractor or a needle driver.

[Joint Function Unit]

The joint function unit 1 includes a base part 11, the movable part 13, a flexible member 15, a drive wire 19, and an elastic body 21.

The base part 11 is a columnar body (particularly a circular columnar body) made of resin, metal, or the like. The base part 11 is attached to a tip of the shaft 5 and constitutes a fixed-side member. The shaft 5 also constitutes a portion of the fixed-side member.

The base part 11 is not limited to a columnar body, and may be a plate-like body or the like, if in the shape of a wall through which the drive wire 19 to be described later is inserted. The base part 11 may be in an appropriate form according to the device to which the joint function unit 1 is applied.

The movable part 13 is a columnar body (particularly a circular columnar body) made of resin, metal, or the like. The movable part 13 is attached to the end effector 7 and constitutes a movable-side member. The end effector 7 also constitutes a portion of the movable-side member.

The movable part 13 is not limited to a columnar body, and may be a plate-like body or the like, if being a member allowing the end effector 7 to be attached thereto. The movable part 13 may also be in an appropriate form according to the device to which the joint function unit 1 is applied.

The movable part 13 like this is supported by the base part 11 so as to be displaceable between a bending position and an extension position with respect to an axial direction by the flexible member 15. The term "axial direction", when used alone, means a direction along an axial center of the joint function unit 1, and may include a slightly inclined direction in addition to a direction strictly parallel to the axial center. The bending position refers to a position where an axis of the movable part 13 intersects the axial direction and bending of the joint function unit 1 is maximum. The extension position refers to a position where the axis of the movable part 13 is along the axial direction. In the extension position, the axis of the movable part 13 does not have to be strictly along the axial direction, and may be slightly shifted.

The flexible member 15 is arranged in the axial center of the joint function unit 1 and displaceably supports the movable part 13 on the base part 11. The flexible member 15 of the present embodiment includes an inner flexible tube 16 and an outer flexible tube 17.

The inner flexible tube 16 is a double coil freely bendable with respect to the axial direction, and includes an outer coil portion 23 and an inner coil portion 25. The inner flexible tube 16 is not limited to one using a double coil if able to displaceably support the movable part 13 on the base part 11.

The outer coil portion 23 and the inner coil portion 25 are coil springs. Both the outer coil portion 23 and the inner coil portion 25 may be made of metal, resin, or the like. A sectional shape of wires of the outer coil portion 23 and the inner coil portion 25 is circular. However, the sectional shape is not limited to circular.

The inner coil portion 25 has a smaller diameter than the outer coil portion 23 and is screwed into the outer coil portion 23. The diameters of the outer coil portion 23 and the inner coil portion 25 are constant from one end to the other end in the axial direction. However, it is also possible to vary the diameter of the outer coil portion 23 in the axial direction.

The outer coil portion 23 has a plurality of gaps (pitches) that separate axially adjacent winding portions from each other in the axial direction. A winding portion of the inner coil portion 25 is fitted into the plurality of gaps from the inside.

The flexible member 15 like this has elasticity enabling bending and restoration of the outer coil portion 23 and the inner coil portion 25 with respect to the axial direction of the coil shape, and, as a whole, has elasticity enabling bending and restoration with respect to the axial direction.

The flexible member 15 is surrounded by the outer flexible tube 17 interposed between the base part 11 and the movable part 13.

The outer flexible tube 17 is composed of a bellows made of a tube having a wavy sectional shape. The outer flexible tube 17 is made of metal, resin, or the like. The outer flexible tube 17 may also be a coil spring or other tubular body. The outer flexible tube 17 is not particularly limited if in the shape of a tube having elasticity.

The outer flexible tube 17 elastically bends and restores in response to displacement of the movable part 13 with respect to the base part 11. Accordingly, the outer flexible tube 17 imparts to the joint function unit 1 a linear load characteristic that a load increases as a bending angle increases. The load characteristic will be described later.

Thus, the flexible member 15 may, by bending and restoring itself, displace the movable part 13 and the end effector 7 with respect to the base part 11 and the shaft 5. Such displacement is performed by the drive wire 19.

The drive wire 19 is a cord-like member made of metal or the like, and is provided in four places in the joint function unit 1 in a circumferential direction at intervals of 90 degrees in the present embodiment. The drive wires 19 facing each other in a radial direction of the joint function unit 1 form a pair. Thus, in the present embodiment, two pairs of drive wires 19 are provided.

However, it is also possible to omit one pair of drive wires 19, and it suffices if the joint function unit 1 includes a plurality of drive wires 19. For example, three drive wires 19 may be provided. In this case, the drive wires 19 are preferably arranged at intervals of 120 degrees in the circumferential direction. The drive wire 19, if being a cord-like member, may be a stranded wire, a nickel-titanium (NiTi) single wire, a piano wire, an articulated rod, a chain, a string, a thread, a rope, or the like.

These drive wires 19 bend the joint function unit 1 by being pulled in the axial direction, and may be directly or indirectly connected to an operation mechanism (not shown) to be operated in the axial direction. Operation in the axial direction means causing the drive wire 19 to advance or retreat in the axial direction.

On one side of each drive wire 19 is provided a fixed part 27 fixed to the movable part 13. Any fixing means may be applied to the fixed part 27.

Each drive wire 19 extends in the axial direction from the fixed part 27 and is inserted through the outer flexible tube 17 and the base part 11, and has the other side thereof passing through the shaft 5. On the other side of the each drive wire 19 is provided a supported part 29.

The supported part 29 is provided on the other side of the drive wire 19 and is a portion supported by the base part 11. The supported part 29 of the present embodiment is a crimping portion at the other end of the drive wire 19 and is joined to an end of a connection wire 31 by crimping. The supported parts 29 of the paired drive wires 19 are connected via the connection wire 31. The paired drive wires 19 may also be integrally provided in a loop shape.

The connection wire 31 has both ends each arranged on the same axis as the other end of the paired drive wires 19 via a guide part 33 to reach the supported part 29. The guide part 33 of the present embodiment is a pulley, and is supported by the shaft 5, an operation mechanism, or the like. It is also possible to omit the connection wire 31 and the guide part 33 and combine the supported part 29 with the operation mechanism.

The elastic body 21 supports the supported part 29 of the drive wire 19 on the base part 11 and energizes the supported part 29 toward a side opposite to the fixed part 27 of the same drive wire 19 in the axial direction. Accordingly, the elastic body 21 applies tension to each drive wire 19 and improves bending rigidity of each drive wire 19.

The elastic body 21 of the present embodiment is composed of a coil spring, particularly a compression spring having a pitch. The elastic body 21 may be made of metal, resin, or the like, and may have an appropriate shape depending on an elastic modulus or the like. For example, in the case of rubber or the like, the elastic body may have a columnar shape or tubular shape.

The elastic body 21 is interposed between the supported part 29 of the drive wire 19 and the base part 11. Specifically, the elastic body 21 is provided for each drive wire 19 and has each drive wire 19 inserted therethrough and arranged on the same axis. Both ends of the elastic body 21 respectively abut against the base part 11 and the supported part 29.

Thus, the elastic body 21 is configured to be arranged in parallel with the drive wire 19 so as to exert elastic force in the axial direction. The term "parallel" used herein refers to arranging the elastic body 21 so that the axial direction and a direction in which the elastic force acts are parallel. However, the two directions do not have to be strictly parallel, and the term "parallel" may also include a case where one of the two directions is slightly inclined with respect to the other. The elastic body 21 between the supported part 29 and the base part 11 may be omitted, and the guide part 33 may be configured to be pulled by the elastic body 21.

Each elastic body 21 has an axial dimension in a free state set smaller than an axial dimension between the supported part 29 and the base part 11. Hence, each elastic body 21 is compressed between the supported part 29 and the base part 11 according to a dimensional difference. Due to this compression, a load is applied to each elastic body 21 and tension corresponding to the load is applied to the drive wire 19.

The elastic body 21 like this, together with the flexible member 15, is able to impart to the joint function unit 1 the linear load characteristic that a load increases as a bending angle increases. The load characteristic will be described later.

[Operation]

(A) and (B) of FIG. 4 are conceptual views of the manipulator of FIG. 1, in which (A) of FIG. 4 shows a normal state and (B) of FIG. 4 shows a bending state.

In the present embodiment, in the normal state in which the drive wire 19 is not operated, tension is applied by the elastic body 21 to the drive wire 19, eliminating looseness and improving bending rigidity in the drive wire 19.

Hence, even if an external force F is applied to the end effector 7 or the movable part 13 of the joint function unit 1, both being the movable-side member, in a direction (left-right direction in (A) of FIG. 4) intersecting the axial direction, unintended displacement of the movable part 13 and the end effector 7 can be suppressed.

When an operator such as a doctor operates the manipulator 3, the joint function unit 1 is bent by pulling any one of the drive wires 19. By combining different pairs of drive wires 19 and pulling the same, it is possible to bend the joint function unit 1 360 degrees in all directions. Accordingly, the end effector 7 can be oriented in a desired direction.

When any one of the drive wires 19 is pulled and the joint function unit 1 is bent, as in (B) of FIG. 4, in an inner portion of the bend, the supported part 29 of the drive wire 19 (referred to as inner wire 19) is displaced so as to widen a space between itself and the base part 11 in the axial direction. Accordingly, the fixed part 27 of the inner wire 19 is pulled toward the base part 11 side.

At this time, since the joint function unit 1 is bent and this state is maintained, the inner wire 19 is subjected to tension greater than that in the normal state. As a result, the inner wire 19 is improved in bending rigidity.

On the other hand, in an outer portion of the bend, as the drive wire 19 (referred to as outer wire 19) paired with the inner wire 19 is pulled by the fixed part 27 as bending occurs, the supported part 29 is displaced and pushed to narrow the space between itself and the base part 11 in the axial direction.

At this time, the elastic body 21 coaxial with the outer wire 19 is compressed against its own elastic force, and the elastic body 21 coaxial with the inner wire 19 attempts to extend between the supported part 29 and the base part 11 by its own elastic force. Hence, even if the supported part 29 is displaced toward the base part 11 side in a direction of losing tension, the outer wire 19 is given tension without loosening. As a result, the outer wire 19 is also improved in bending rigidity, together with the inner wire 19.

In this way, in the manipulator 3 of the present embodiment, even during bending in which the drive wire 19 is operated, the bending rigidity of the drive wire 19 is improved on the inside and outside of the bend.

Hence, even if the external force F is applied to the end effector 7 or the movable part 13 of the joint function unit 1 in a direction (up-down direction in (B) of FIG. 4) intersecting the axial direction, unintended displacement of the end effector 7 can be suppressed.

An operation force for compressing the elastic body 21 coaxial with the outer wire 19 can be assisted by the elastic force for extending the elastic body 21 coaxial with the inner wire 19. Hence, an increase in overall operation force for bending the joint function unit 1 can be suppressed, and the joint function unit 1 can be easily bent.

[Displacement Characteristic]

FIG. 5 is a graph showing a relationship between displacement amount with respect to external force and load of an elastic body.

FIG. 5 is obtained by measuring a displacement amount of the end effector 7 when the external force F of 2N is applied to the end effector 7 in a direction intersecting the axial direction in the normal state. The load in FIG. 5 indicates a load applied to the elastic body 21 in the normal state.

As in FIG. 5, during from a state in which no load is applied to the elastic body 21 until the magnitude of the load of the elastic body 21 becomes equal to the external force F, a ratio of decrease in the displacement amount of the end effector 7 is large. On the other hand, even if the load of the elastic body 21 exceeds the external force F, the ratio of decrease in the displacement amount is reduced. As the load of the elastic body 21 is increased, the bending rigidity of the drive wire 19 is improved and it becomes difficult to bend the joint function unit 1. Thus, the load of each elastic body 21 is preferably set equivalent to the assumed external force F.

[Load Characteristic]

FIG. 6 is a graph showing a relationship between load and bending angle of a joint function unit. FIG. 6 shows a load of the joint function unit 1, the flexible member 15 and the drive wire 19 when the paired drive wires 19 are operated to bend the joint function unit 1 from a bending angle of 0 degree to the bending angle of 90 degrees and then return the joint function unit 1 to the bending angle of 0 degree.

In the present embodiment, the elastic body 21 and the flexible member 15 have a linear load characteristic in which the load increases as the bending angle increases, and the joint function unit 1 has a linear load characteristic in which the elastic body 21 and the flexible member 15 are combined.

Thus, the joint function unit 1 has excellent load resistance and bendability. By adjusting the load characteristic of the elastic body 21 and the flexible member 15, the load characteristic of the joint function unit 1 can be adjusted and set.

Effects of Embodiment 1

As described above, in the present embodiment, the joint function unit 1 is provided in which the movable part 13 is supported so as to be displaceable between the bending position and the extension position with respect to the base part 11. The joint function unit 1 includes: a plurality of drive wires 19, having the fixed part 27 fixed to the movable part 13 on one side in the axial direction and the supported part 29 supported by the base part 11 on the other side in the axial direction; and the elastic body 21, supporting the supported part 29 of the plurality of drive wires 19 on the base part 11, energizing the supported part 29 toward a side opposite to the fixed part 27 in the axial direction, and applying tension to the drive wire 19.

Thus, in the present embodiment, since looseness in the drive wire 19 is eliminated and bending rigidity is improved in response to the tension applied by the elastic body 21, even if the external force F acts on the movable part 13 or the end effector 7, unintended displacement of the movable part 13 or the end effector 7 can be suppressed.

Since the elastic body 21 is arranged in parallel with the plurality of drive wires 19, the elastic body 21 is able to easily and reliably apply tension to the drive wires 19.

The plurality of drive wires 19 are each inserted through the base part 11 between the fixed part 27 and the supported part 29. The elastic body 21 is interposed between the supported part of the plurality of drive wires 19 and the base part 11.

Thus, in the present embodiment, tension can be applied to the drive wire 19 by a simple configuration.

Since the elastic body 21 has each of the plurality of drive wires 19 inserted therethrough and provided on the same axis, the elastic body 21 can be held between the supported part 29 and the base part 11 by a simple configuration.

Embodiment 2

FIG. 7 is a conceptual view showing a manipulator to which a joint function unit according to Embodiment 2 of the present invention is applied. In Embodiment 2, the configurations corresponding to those of Embodiment 1 are assigned the same reference numerals, and repeated descriptions are omitted.

In Embodiment 2, a single elastic body 21 is used for the paired drive wires 19 of the joint function unit 1. Specifically, a support member 35 is provided spanning between the supported parts 29 of the paired drive wires 19, and the elastic body 21 is interposed between the support member 35 and the base part 11. The others are the same as those of Embodiment 1.

The support member 35 is a plate-like body provided spanning between the supported parts 29 of the paired drive wires 19. The drive wire 19 is inserted through the support member 35. The support member 35 is pressed against the supported part 29 by the elastic body 21.

In Embodiment 2, the same effects as those of Embodiment 1 can be achieved.

Embodiment 3

FIG. 8 is a conceptual view showing a manipulator to which a joint function unit according to Embodiment 3 of the present invention is applied. In Embodiment 3, the configurations corresponding to those of Embodiment 1 are assigned the same reference numerals, and repeated descriptions are omitted.

In Embodiment 3, the paired drive wires 19 of the joint function unit 1 are connected by the elastic body 21. Specifically, the guide part 33 is provided that guides one of the paired drive wires 19 and locates the supported part 29 of the paired drive wires 19 on the same axis. The elastic body 21 connects between the supported parts 29 of the paired drive wires 19. The others are the same as those of Embodiment 1.

The guide part 33 is configured in the same manner as in Embodiment 1. One of the paired drive wires 19 is formed longer than the other of the paired drive wires 19, and is wound around the guide part 33 so that the supported parts 29 of two drive wires 19 are located on the same axis.

In the present embodiment, a pair of elastic bodies 21 are provided and are each joined to the supported part 29. The elastic bodies 21 are connected by a pair of connecting members 37. The connecting member 37 is a member to which the elastic body 21 is integrally joined. These connecting members 37 are engaged by a clamping part 37a clamping a drive shaft 39.

The elastic body 21 energizes the connecting member 37 in a direction in which the drive shaft 39 is clamped by the clamping part 37a, and holds the state in which the drive shaft 39 is clamped by the clamping part 37a. The drive shaft 39 is connected to an operation mechanism and is displaced in the axial direction in response to an operation of the operation mechanism.

Thus, in Embodiment 3, the same effects as those of Embodiment 1 can be achieved.

Embodiment 4

FIG. 9 is a conceptual view showing a manipulator to which a joint function unit according to Embodiment 4 of the present invention is applied, (A) of FIG. 10 is a conceptual view showing a modification of Embodiment 4, and (B) of FIG. 10 is a conceptual view of (A) of FIG. 10 as seen from a direction 90 degrees different from that of (A) of FIG. 10. In Embodiment 4, the configurations corresponding to those of Embodiment 1 are assigned the same reference numerals, and repeated descriptions are omitted.

In Embodiment 4, the flexible member 15 of the joint function unit 1 is composed of a universal joint. The others are the same as those of Embodiment 1. The flexible member 15 is not limited to a universal joint if composed of a plurality of mutually swingable members that are connected to each other. For example, as in (A) and (B) of FIG. 10, it is also possible to swingably connect a first swinging member 40a with respect to the base part 11, swingably connect a swinging member 40b in an orthogonal direction with respect to the first swinging member 40a, and join the movable part 13 to the swinging member 40b.

In Embodiment 4, the same effects as those of Embodiment 1 can be achieved. In Embodiment 4, a linear load characteristic can be imparted by the elastic body 21 to the joint function unit 1 that does not have a linear load characteristic.

Embodiment 5

FIG. 11 is a conceptual view showing a manipulator to which a joint function unit according to Embodiment 5 of the present invention is applied. In Embodiment 5, the configurations corresponding to those of Embodiment 1 are assigned the same reference numerals, and repeated descriptions are omitted.

In Embodiment 5, the elastic body 21 is provided between a support part 41 of the shaft 5 as the fixed-side member and the supported part 29 of the drive wire 19. Specifically, the shaft 5 includes the support part 41 located on a side opposite to the fixed part 27 with the supported part 29 of each drive wire 19 therebetween in the axial direction. The elastic body 21 is interposed between the support part 41 and the supported part 29.

In Embodiment 5, the connection wire 31 and the guide part 33 are omitted, and the supported part 29 is combined with an operation mechanism. By this combination, tension is applied to the drive wire 19 in the present embodiment. However, the connection wire 31 and the guide part 33 may be provided as in Embodiment 1. The others are the same as those of Embodiment 1.

The support part 41 may be provided at an end of the shaft 5 or inside the shaft 5. The support part 41 may have any shape if able to support the elastic body 21. The elastic body 21 of the present embodiment is a tension spring.

In Embodiment 5 like this, the same effects as those of Embodiment 1 can be achieved.

The invention claimed is:

1. A joint function unit in which a movable-side member is supported so as to be displaceable between a bending position and an extension position with respect to a fixed-side member, the joint function unit comprising:
   a plurality of drive wires, having a fixed part fixed to the movable-side member on one side in an axial direction and a supported part supported by the fixed-side member on the other side in the axial direction; and
   an elastic body, configured to support the supported part of the plurality of drive wires on the fixed-side member, energize the supported part toward a side opposite to the fixed part in the axial direction, and apply tension to the plurality of drive wires, wherein
   each of the plurality of drive wires is inserted through the fixed-side member between the fixed part and the supported part, and
   the elastic body is interposed between and abuts against the supported part of the plurality of drive wires and the fixed-side member.

2. The joint function unit according to claim 1, wherein the elastic body is arranged in parallel with the plurality of drive wires.

3. The joint function unit according to claim 1, wherein the elastic body has each of the plurality of drive wires inserted therethrough and provided on a same axis.

4. The joint function unit according to claim 1, further comprising:

a support member, spanning between the supported parts of the plurality of drive wires, wherein
the elastic body is interposed between the support member and the fixed-side member.

5. The joint function unit according to claim 1, further comprising:
a guide part, guiding one of the plurality of drive wires and locating the supported part of the plurality of drive wires on a same axis, wherein
the elastic body connects between the supported parts of the plurality of drive wires.

6. The joint function unit according to claim 1, wherein
the fixed-side member comprises a support part located on a side opposite to the fixed part with the supported part of the plurality of drive wires therebetween in the axial direction; and
the elastic body is interposed between the support part and the supported part of the plurality of drive wires.

7. The joint function unit according to claim 1, wherein the elastic body is a coil spring.

8. The joint function unit according to claim 1, wherein
the plurality of are drive wires operate the supported part in the axial direction to displace the movable-side member with respect to the fixed-side member.

9. The joint function unit according to claim 2, further comprising:
a guide part, guiding one of the plurality of drive wires and locating the supported part of the plurality of drive wires on a same axis, wherein
the elastic body connects between the supported parts of the plurality of drive wires.

10. The joint function unit according to claim 2, wherein
the fixed-side member comprises a support part located on a side opposite to the fixed part with the supported part of the plurality of drive wires therebetween in the axial direction; and
the elastic body is interposed between the support part and the supported part of the plurality of drive wires.

* * * * *